United States Patent [19]

Lin et al.

[11] Patent Number: 5,321,193
[45] Date of Patent: Jun. 14, 1994

[54] SKELETAL ISOMERICATION OF OLEFINS WITH AN ALUMINA BASED CATALYST

[75] Inventors: Chih-Cheng Lin; Hung-Ming Yang; Chong-Chien Lai; Chien-Chung Chang; Larry L. K. Kuo; Kun-Yung Tsai, all of Taipei, Taiwan

[73] Assignee: Chinese Petroleum Corporation, Taipei, Taiwan

[21] Appl. No.: 748,347

[22] Filed: Aug. 22, 1991

Related U.S. Application Data

[63] Continuation-in-part of Ser. No. 684,097, Apr. 12, 1991, abandoned.

[51] Int. Cl.$^5$ .......................... C07C 5/22; C07C 5/27; B01J 21/02
[52] U.S. Cl. ........................ 585/671; 585/664; 502/355
[58] Field of Search ............... 585/671, 664; 502/355, 502/202

[56] References Cited

U.S. PATENT DOCUMENTS

| | | | |
|---|---|---|---|
| 2,422,884 | 6/1947 | Burgin | 585/671 |
| 4,200,552 | 4/1980 | Noguchi et al. | 252/466 PT |
| 4,225,419 | 9/1980 | Myers | 208/135 |
| 4,707,767 | 11/1987 | Cheng et al. | 502/167 |
| 5,043,523 | 8/1991 | Hsing | 585/664 |

Primary Examiner—Asok Pal
Assistant Examiner—P. Achutamurthy
Attorney, Agent, or Firm—Browdy and Neimark

[57] ABSTRACT

A process for the skeletal isomerization of olefins wherein the olefins are contacted with a SKISO-11 alumina base catalyst to convert into isomerized products effectively under the conversion conditions comprising a temperature of above 200° C. to about 650° C., the pressure of 0.3 to about 10 atmospheres and a molar ratio of hydrogen or nitrogen to olefins feed from 0 to about 10.

8 Claims, 1 Drawing Sheet

SKELETAL ISOMERICATION OF OLEFINS WITH AN ALUMINA BASED CATALYST

This is a continuation-in-part application of copending parent application, Ser. No. 07/684,097, filed Apr. 12, 1991, now abandoned the contents of which are hereby incorporated by reference

FIELD OF THE INVENTION

This invention relates to the preparation of the skeletal isomerization catalyst which permits the isomerization of normal olefins to their isomers. Specifically, this invention relates to the skeletal isomerization as well as double bond isomerization of four to twenty carbon-number olefins. This invention more particularly relates to the conversion of linear alkenes into branched alkenes having the same carbon numbers. The catalyst in this invention is prepared by impregnation, then calcination and activation steps, to form a composition of the catalyst named as SKISO-11, an oxide of aluminum or oxides of aluminum and boron supported on active alumina in pellet form.

BACKGROUND OF THE INVENTION

In general, the double-bond isomerization reaction of olefins often occurs in the presence of an acidic catalyst by proton transfer between olefins. However, it is not necessary to proceed with the reaction at high temperature. Skeletal isomerization of olefins is known to be conducted by contacting unbranched olefins with acidic catalysts at more extreme conditions. Therefore, for skeletal isomerization of olefins, the alkyl carbonium ion which is the transition state of double-bond isomerization reaction needs to undergo a rearrangement, and subsequently a proton transfer step to form the desired products.

In the past, the skeletal isomerization catalysts were mostly prepared from an alumina support with some modifications on the surface by halogen-containing compounds, such as HBr or butyl bromide. Examples are: Sun U.S. Pat. No. 4,778,943, issued Oct. 18, 1988; Sun U.S. Pat. No. 4,654,463, issued Mar 31, 1987; and Elazar et al U.S. Pat. No. 4,433,191, issued Feb. 21, 1984. The catalyst in this invention is prepared without any modification of halide compound on the catalyst surface and can be effectively employed for the skeletal isomerization of olefins.

The isomerization reaction of olefins is well known to be limited by the thermodynamic equilibrium of reacting species. The skeletal isomerization catalysts described in some patents or published papers were mostly prepared from the treatment of halogen-containing compounds in order to maintain the activity and the selectivity. However, there are some disadvantages for those catalysts, such as excessively high capital costs, undue waste, difficulty of treatment, etc.

The product of skeletal isomerization for $C_4$ olefin is isobutylene which is one of the feedstock reagents for producing methyl tertiary butyl ether (MTBE), an ether compound with high octane number used in gasoline. For the skeletal isomerization of $C_5$ olefin, the desired product is isoamylene which is the feedstock reagent for producing tertiary amyl methyl ether (TAME), also a high octane-number compound.

SUMMARY OF THE INVENTION

Hence, the present invention has a use for improving the quality of gasoline. An objective of this invention is to provide a new catalyst for which the cost of the process investment can be reduced and the skeletal isomerization of normal olefins can proceed effectively.

It has now been discovered according to the present invention that the skeletal isomerization of olefins which are characterized in having from 4 to about 20 carbon atoms per molecule can proceed via the action of SKISO-11 catalyst, an oxide of aluminum or oxides of aluminum and boron supported on the surface of gamma- or eta- alumina pellets. The olefin isomers of the main product would be near the equilibrium compositions, either for $C_4$, $C_5$ olefins or for other carbon-number olefins. The activity and selectivity characteristics of such catalyst employed in the reaction of the present invention are superior to other halogenated gamma-alumina catalysts, such as brominated or fluorinated gamma-alumina base catalysts.

BRIEF DESCRIPTION OF DRAWING

The sole figure (FIG. 1) is a schematic flow diagram showing a process for preparing the catalyst of the present invention.

DETAILED DESCRIPTION OF THE INVENTION

Figure 1:
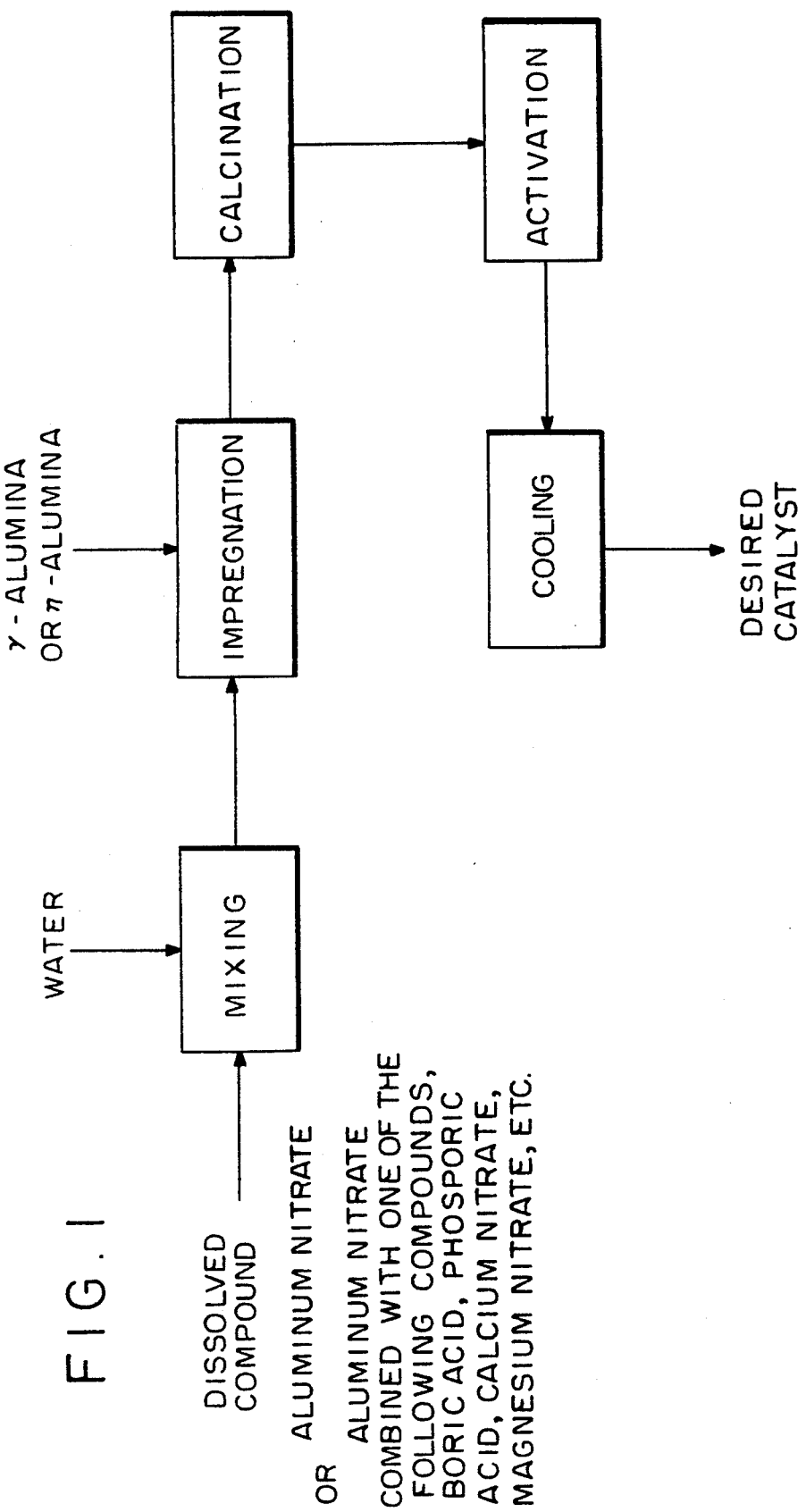

Normal olefins are converted into iso-olefins in the presence of the SKISO-11 catalyst of this invention. The support used in the catalyst is any crystalline type of alumina, except alpha type, preferably eta- or gamma- alumina, with the surface area of above 40 to about 500 m²/gram (as measured by the BET method using $N_2$). Other inorganic oxides may be used in the catalyst of this invention. However, the catalyst of this invention should contain at least 60 mole % of gamma-alumina or eta-alumina. Other supports, such as zeolite, can also be used. The catalyst should contain an oxide of aluminum, which is not a crystalline type, from about 0.01 to about 20 wt %, preferably from 0.03 to about 11 wt %, based on the total catalyst weight. The catalyst can also contain the oxide of aluminum combined with an oxide of phosphorus, boron, calcium, or magnesium. Thus the catalyst in this invention can be formulated as $Al_2O_3$/gamma-(or eta-)alumina or $Al_2O_3/M_xO_y$/gamma-(or eta-)alumina, wherein the subscripts x and y respectively equal 1 or 2 and 1 to 5. The character M represents boron, phosphorus, calcium, and magnesium, etc. The composition of such mixed oxides should be in the range of 0.01 to 20 wt % based on total catalyst weight. The preparation method for such catalyst as well as its application to the skeletal isomerization of normal olefins and the resulting mixture are disclosed below. Typically, the catalyst of this invention can be utilized in the skeletal isomerization of olefins to convert n-butenes into isobutylene or to convert n-pentenes into isoamylenes, within which the reaction can be double bond or skeletal isomerization.

The preparation method of the catalyst and the reaction for $C_4$ or $C_5$ olefins are described as follows.

According to this invention, the characteristics of the preparation process for the catalyst are:

1. The active alumina pellet is impregnated in an acidic aqueous solution which is aluminum nitrate with the concentration in the range of 0.001 M to 1.0 M. The aqueous solution can also be composed of aluminum nitrate and boric acid or aluminum nitrate and phosphoric acid, or calcium nitrate with the total concentration of 0.001 M to 1.0 M. Preferably the concentration of such compounds in the aqueous solution is in the range of 0.003 M to 0.1 M.

2. The impregnation process is desirably carried out at temperature in the range of 20 to 90 ° C. for 0.5 to 20 hours.

3. After impregnation, the solid catalyst is separated and then calcined under air for 2 to 30 hours at temperature in the range of 300 to about 800° C.

4. After calcination, the catalyst is then activated under air or nitrogen or hydrogen for 2 to 30 hours at temperature in the range of 300 to about 800° C.

5. After activation, the catalyst is then cooled down to room temperature to form the desired catalyst.

The above preparation process is also depicted in FIG. 1. Using the above preparation method, the present catalyst can thus be formulated as described above.

In use, the feedstock for skeletal isomerization contains at least one alkene, preferably an alkene having from 4 to 8 carbon numbers per molecule. The alkene may have internal or terminal double bonds. The normal alkenes may contain other hydrocarbons having the same numbers of carbon atoms, such as alkanes. Particular feedstocks for use in this invention are fractions containing butenes, or mixture of butenes with isobutylene, mixture of pentenes with isoamylenes. Such fractions are commonly produced in petroleum refineries or petrochemical plants, for example, $C_5$ stream from naphtha cracker and $C_4$ stream from MTBE plant.

The olefinic feedstocks can contain inert diluents with the content of alkenes in the range of above 10 to 95 wt % of the feed stream.

The typical example of the application of the catalyst is in the isomerization reactions, either double bond or skeletal isomerization, of the $C_4$ or $C_5$ olefins. The term $C_4$ olefin refers to the follow olefins: 1-butene, cis-2-butene, trans-2-butene and isobutylene. The term $C_5$ olefin refers to the following olefins: 1-pentene, cis-2-pentene, trans-2-pentene, 3-methyl-1-butene, 2-methyl-1-butene and 2-methyl-2-butene. The catalyst is regenerable by heating in an oxygen and nitrogen-containing gas at temperature in the range of above 300° C. to about 800° C. For maintaining the activity of the catalyst, a hydrogen or nitrogen gas is incorporated in the reaction mixture with a molar ratio of gas to the reaction mixture from zero to about ten, preferably a molar ratio of 0 to 5. The experimental apparatus and procedure are summarized below.

The catalyst is placed in a fixed-bed reactor which has an inner diameter of 2.54 cm and a length of 30.5 cm. Some inert solid particles are placed in lower and upper ends of the reactor to support the catalyst and to make uniform distributions of the reaction stream within the reactor. The experimental apparatus also includes feed pump, heating medium, product collecting and sampling units, mass flow meter and temperature controlled system, etc. The product is analyzed by gas chromatography, e.g. using a Carlo Erba GC 6000 Vega Series unit with FID detector. The column is a capillary type column.

The invention is further illustrated by the following examples which are descriptive but not limitative.

EXAMPLE 1

Catalyst Preparation

A catalyst was prepared as follows. 1.0 g of aluminum nitrate was dissolved in water to form an aqueous solution with a molar concentration of aluminum nitrate of 0.0267 M. A gamma-alumina support was impregnated with such an aqueous solution at the temperature of 35° C. for 12 hours. The solid particles were then separated and calcined under air at the temperature of 550° C. for 12 hours. The calcined catalyst was activated under air or hydrogen at a temperature of 500° C. for 4 hours and then cooled to room temperature to form the desired catalyst. The catalyst is thus composed of 0.136 wt % of aluminum oxide supported on gamma-alumina.

EXAMPLE 2

Catalyst Preparation

Another formulation of the catalyst is obtained by the preparation procedure as follows: 0.3 g of aluminum nitrate and 0.5 g of boric acid were dissolved in water to form an aqueous solution with the molar concentrations of aluminum nitrate and boric acid of 0.008 M and 0.081 M, respectively. The gamma-alumina support was then impregnated with such an aqueous solution at 40° C. for 20 hours. The solid particles were then separated and calcined at the temperature of 550° C. for 12 hours. The calcined catalyst was then activated and cooled using the same conditions as described in EXAMPLE 1. The desired catalyst is thus gamma-alumina.

EXAMPLE 3

Skeletal Isomerization

1-Pentene with above 95 % of purity was used as the feed. The catalyst used was 5.5 grams of $Al_2O_3$/gamma-alumina. Under the reaction condition of temperature at 450° C., one atmosphere and weight hourly space velocity (WHSV) of 0.8 hr 1, the product distribution is obtained as 3.1 wt% of 3-methyl-1-butene, 17.2 wt% of trans-2-pentene, 9.1 wt% of cis-2-pentene, 3.1 wt% of 2-methyl-2-butene and 2-methyl-1-butene (that is, isoamylenes), 6.5 wt % of pentenes and $C_4$ (−) and 1.0 wt % of $C_6$ (+) hydrocarbons. The conversion of n-pentenes and the selectivity of isoamylene were estimated as 0.737 and 0.856, respectively. If pentenes content in the product is normalized and compared with the equilibrium compositions of $C_5$ olefins which are estimated thermodynamically, a consistent result is obtained as shown in Table I.

TABLE I

The comparison of olefin composition with its equilibrium composition

| | Composition (wt %) | |
|---|---|---|
| Component | C5 Product | Equilibrium |
| 1-Pentene | — | 4.06 |
| Trans-2-pentene | 18.59 | 12.21 |
| Cis-2-pentene | 9.84 | 9.07 |
| Isoamylenes | 68.22 | 70.82 |
| 3-Methyl-1-butene | 3.35 | 3.84 |

EXAMPLE 4

Skeletal Isomerization

Another typical example was carried out for the skeletal isomerization of n-butene. 99.5 wt % of 1-butene was used as the feed to convert into its isomers. The catalyst used was 5.5 grams of $Al_2O_3/B_2O_3$/gamma-alumina. Under the reaction condition of temperature at 450° C., one atmosphere and WHSV at 1.0 hr$^{-1}$, the product distribution obtained was 15.4 wt % of 1-butene, 23.9 wt % of trans-2-butene, 17.1 wt% of cis-2-butene, 32.9 wt % of isobutylene, 4.8 wt % of butane and $C_3(-)$ and 5.9 wt % of $C_5(+)$ hydrocarbons. The conversion of n-butenes and the selectivity of isobutylene were estimated as 0.436 and 0.755, respectively. Normalizing butenes in the product, the composition is thus very consistent with the equilibrium composition of $C_4$ olefin which is also estimated thermodynamically. The compared result is shown in Table II.

TABLE II

The comparison of $C_4$ olefin composition with its equilibrium composition

| Component | Composition (wt %) | |
|---|---|---|
| | C4 Product | Equilibrium |
| 1-Butene | 17.2 | 15.4 |
| Trans-2-butene | 26.8 | 26.6 |
| Cis-2-butene | 19.1 | 18.3 |
| Isobutylene | 36.9 | 39.7 |

EXAMPLE 5

Skeletal Isomerization

The feed was above 95 wt % of 1-pentene. The catalyst used was 5.5 grams of $Al_2O_3$/gamma-alumina. The operating conditions were one atmosphere, WHSV at 0.81 hr$^{-1}$ and different temperatures, such as 200, 250, 300, 350, 400 and 450° C. The composition of product for each condition is shown in Table III.

TABLE III

The product composition of $C_5$ skeletal isomerization for different operating temperature.

| Component | Composition (wt %) at Reaction Temperature (°C.) | | | | | |
|---|---|---|---|---|---|---|
| | 200 | 250 | 300 | 350 | 400 | 450 |
| Pentane + C4 (−) | 0.9 | 1.5 | 1.7 | 3.6 | 6.4 | 6.5 |
| 1-Pentene | 17.4 | — | — | — | — | — |
| Trans-2-pentene | 58.4 | 60.0 | 52.6 | 35.7 | 19.9 | 17.1 |
| Cis-2-pentene | 23.3 | 25.9 | 24.4 | 17.4 | 10.1 | 9.1 |
| Isoamylenes | — | 12.6 | 21.0 | 41.2 | 59.9 | 63.1 |
| 3-Methyl-1-butene | — | — | 0.3 | 1.2 | 2.5 | 3.1 |
| C6 (+) | — | — | — | 0.9 | 1.2 | 1.1 |

EXAMPLE 6

Skeletal Isomerization

The feed was 99.5 wt % of 1-butene and the catalyst used was $Al_2O_3$/gamma-alumina. The operating conditions were selected as at one atmosphere ad WHSV at 1.0 for different temperatures, 250, 300, 350, 400 and 500° C. The yield of isobutylene is different for various temperatures. A quick increase of isobutylene yield occurred at 400° C. reaction temperature. The composition of product for each condition is shown in Table IV.

TABLE IV

The product composition of $C_4$ skeletal isomerization for different operating temperature.

| Component | Composition (wt %) at Reaction Temperature (°C.) | | | | | |
|---|---|---|---|---|---|---|
| | 250 | 300 | 350 | 400 | 450 | 450 |
| Butane + C3 (−) | 0.2 | 0.3 | 0.9 | 4.9 | 5.0 | 9.5 |
| 1-Butene | 21.7 | 20.0 | 19.2 | 17.1 | 14.9 | 15.4 |
| Trans-2-butene | 41.5 | 47.8 | 46.5 | 33.2 | 24.7 | 22.0 |

TABLE IV-continued

The product composition of $C_4$ skeletal isomerization for different operating temperature.

| Component | Composition (wt %) at Reaction Temperature (°C.) | | | | | |
|---|---|---|---|---|---|---|
| | 250 | 300 | 350 | 400 | 450 | 450 |
| Cis-2-butene | 36.6 | 31.6 | 30.8 | 23.1 | 17.9 | 16.2 |
| Isobutylene | — | 0.3 | 2.2 | 17.3 | 31.9 | 31.9 |
| C5 (+) | — | — | 0.4 | 4.4 | 5.6 | 5.0 |

Substantially equivalent results were obtained when the operating conditions other than described above were used.

The foregoing description of the specific embodiments will so fully reveal the general nature of the invention that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

What is claimed is:

1. A catalyst for skeletal isomerization of olefins consisting essentially of amorphous alumina supported on a pellet of gamma- alumina or eta-alumina, or amorphous alumina and boria supported on a pellet of gamma-alumina or eta-alumina, which catalyst is manufactured by impregnating a base of gamma- or eta alumina with an aqueous solution of aluminum nitrate or an aqueous solution of aluminum nitrate and boric acid at a total concentration in the range of 0.001 M to 1.0 M for about 0.5 to 20 hours at ambient temperature;

removing the aqueous solution and then drying the solid particles at 140° to 160° C. for 3 to 5 hours; calcining and activating said calcined product by heating said product from 2 to 30 hours at a temperature of 300 to about 800° C.; and then cooling to form the desired catalyst.

2. The catalyst according to claim 1 wherein the content of the total amorphous oxides is in the range of 0.01 to 20.0 weight percent based upon the total catalyst weight.

3. The catalyst according to claim 1 wherein the catalyst has BET surface area in the range of 120 to 300 m$^2$/g, particle size in the range 1.5 to 3.0 mm, pore size in the range of 20 to 100 A.

4. In a process for the skeletal isomerization and double bond isomerization of olefins in a feedstock having from 4 to about 20 atoms per molecule in the presence of a catalyst under isomerization conditions the improvement wherein said catalyst is an alumina base catalyst according to claim 1, wherein the feedstock contains at least one normal olefin with the content of total normal olefins in the range of 8.0 to 99.5 weight %.

5. Process according to claim 4 wherein said olefins are $C_4$ olefins and the product is isobutylene.

6. Process according to claim 4 wherein said olefins are $C_5$ olefins and the product is isoamylenes.

7. Process according to claim 5 wherein the operating conditions for $C_4$ olefins isomerization are: reaction temperature of 100 to 650° C., pressure of one to about 10 atmospheres, WHSV in a range of 0.1 to 15.0 hr.$^{-1}$, the molar ratio of nitrogen or hydrogen gas to reacting mixture in the range of zero to ten.

8. Process according to claim 6 wherein the operating conditions for $C_4$ isomerization are: at reaction temperature of 100 to 650° C., at one to about 10 atmospheres, at WHSV in the range of 0.1 to 10.0 hr.$^{-1}$, the molar ratio of nitrogen or hydrogen gas to reacting mixture in the range of zero to ten.

* * * * *